(12) United States Patent
Harper et al.

(10) Patent No.: US 10,830,765 B1
(45) Date of Patent: Nov. 10, 2020

(54) POINT-OF-CARE DEVICE FOR THE COLORIMETRIC DETERMINATION OF L-PHENYLALANINE IN BIOLOGICAL SAMPLES

(71) Applicant: Analytical Diagnostic Solutions, Inc., Mount Laurel, NJ (US)

(72) Inventors: Robert Harper, Mount Laurel, NJ (US); Jordan Seville, Delran, NJ (US); Amy Bendell, Philadelphia, PA (US)

(73) Assignee: ANALYTICAL DIAGNOSTIC SOLUTIONS, INC., Mount Laurel, NJ (US)

( * ) Notice: Subject to any disclaimer, the term of this patent is extended or adjusted under 35 U.S.C. 154(b) by 156 days.

(21) Appl. No.: 16/139,916

(22) Filed: Sep. 24, 2018

Related U.S. Application Data

(60) Provisional application No. 62/561,854, filed on Sep. 22, 2017.

(51) Int. Cl.
*C12Q 1/00* (2006.01)
*G01N 33/52* (2006.01)
*G01N 21/29* (2006.01)
*G01N 21/31* (2006.01)
*C12Q 1/32* (2006.01)

(52) U.S. Cl.
CPC .............. *G01N 33/526* (2013.01); *C12Q 1/32* (2013.01); *G01N 21/29* (2013.01); *G01N 21/314* (2013.01); *C12Y 104/0102* (2013.01); *C12Y 106/02002* (2013.01); *C12Y 106/99001* (2013.01); *G01N 2021/3181* (2013.01); *G01N 2333/90209* (2013.01); *G01N 2800/50* (2013.01); *G01N 2800/7076* (2013.01)

(58) Field of Classification Search
CPC ...................................................... G01N 33/523
See application file for complete search history.

(56) References Cited

U.S. PATENT DOCUMENTS

2007/0122867 A1   5/2007   Shunnarah et al. ............ 435/27

FOREIGN PATENT DOCUMENTS

WO    WO-2004091376 A2  * 10/2004    ........... G01N 33/526

* cited by examiner

*Primary Examiner* — Bin Shen
(74) *Attorney, Agent, or Firm* — Licata & Tyrrell P.C.

(57) ABSTRACT

Methods and devices for testing and monitoring L-phenylalanine in biological samples are provided.

20 Claims, 4 Drawing Sheets

POINT-OF-CARE DEVICE FOR THE COLORIMETRIC DETERMINATION OF L-PHENYLALANINE IN BIOLOGICAL SAMPLES

This patent application claims the benefit of priority from U.S. Application Ser. No. 62/561,854 filed Sep. 22, 2017, the content of which is herein incorporated by reference in its entirety.

FIELD OF THE INVENTION

The present invention relates to methods and devices for testing and monitoring L-phenylalanine in biological samples.

BACKGROUND OF THE INVENTION

Phenylketonuria (commonly known as PKU) is an inherited disorder that causes a toxic buildup of the amino acid L-phenylalanine (Phe) in the blood. PKU is the most common disorder of amino acid metabolism and occurs in 1 out of every 8,000 newborns globally. Most cases of PKU are detected by newborn screening in developed countries shortly after birth, and treatment is typically started promptly. Once newborns are diagnosed with PKU, L-phenylalanine levels must be monitored frequently to ensure they fall within acceptable levels (2-6 mg/dL). Without proper monitoring and treatment, affected infants can develop permanent intellectual disabilities. Seizures, delayed development, behavioral problems, and psychiatric disorders are also common side effects. The testing guidelines are as follows: infants <4 weeks old should be tested 1-2 times per week; infants 4-12 weeks old should be tested 1 time per week; children 1-2 years and older should be tested 2-4 times per month; women who are pregnant should be tested 1-2 times per week; and patients who are ill should be tested 1 time per week as directed by their clinician.

SUMMARY OF INVENTION

The invention describes a colorimetric assay, referred to herein as the "PKU Now", and methods for use of this assay for the quantitative determination of L-phenylalanine (Phe) in biological specimens. A combination of components is comprised to elicit a measurable colored end-product from the application of a biological sample containing the substrate Phe, which is either absent, insufficiently present, or in excess in the biological sample. The assay requires less than 25 µL of blood, saliva, or urine. The end-color of the reagent layer is proportional to the concentration of Phe in the biological sample. This invention is quantitative, faster, more rugged, and easier to perform than analogous wet chemistry assays and lateral flow assays. It can be used at the point-of-care, at home, in the hospital, or at a clinician's office to measure L-phenylalanine and for the diagnose phenylketonuria (PKU).

DETAILED DESCRIPTION OF THE INVENTION

The present invention relates to a unique test strip coupled with an analyzer for the determination of L-phenylalanine (Phe) in biological fluids.

Figure 5:
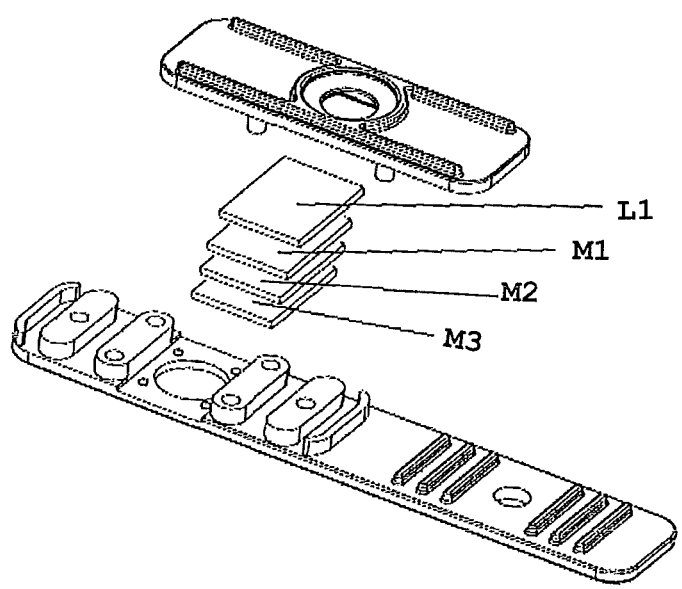
FIG. 5 is a diagram of a non-limiting embodiment of a test strip of the present invention within the top and bottom of a cassette.

The test strip of the present invention is comprised of at most four superimposed layers. The membrane layers can be adhered to a base material through lamination with adhesives or through compression in a cassette with a top and bottom as depicted in FIG. 5, without the requirements of lamination. The multiple stacked membranes comprising the test strip of the present invention are useful for the quantitative detectable change in response to the presence of Phe in a biological sample. Typically, the biological sample is whole blood taken from a patient's finger or heel-stick. In one non-limiting embodiment, the combination of layers in the test strip allows for zero percent bias in the range of 32 to 60% hematocrit and in the analytical range of 0 to 25 mg/dL L-phenylalanine. Accordingly, this invention can be used for both the initial diagnosis of PKU and for monitoring Phe levels in individuals on restricted diets or medications. Neonates often have a hematocrit greater than 55%. Because of this, the present invention is particularly useful in diagnosing PKU in neonates.

As shown in FIG. 5, the test strip comprises four layers, 3 of which are membranes. The first layer depicted in FIG. 5 is sample spreading layer L1. The sample spreading layer is capable of distributing or metering the sample's biological cells evenly across the surface of the primary membrane. The spreading layer provides a uniform concentration of cells between the interface of the spreading layer and the primary membrane. The spreading layer can be a mesh material, an isotropically porous membrane (same porosity throughout), or an anisotropic membrane (a gradient in porosity). The spreading layer can be composed of nylon or polyester with a pore size in the range of 10-300 µm. Precise permeability of the spreading layer is critical, as it determines whether or not a homogeneous biological sample will be uniformly distributed across the surface of the primary membrane layer. The surface of the spreading layer is in direct contact with the primary membrane for uniform transfer of the biological material through a lateral and vertical migration of the biological fluid.

As shown in FIG. 5, the test strip further comprises a primary Membrane-1 M1. The biological fluid flows transverse across the spreading layer before migrating vertically into the primary membrane. The primary membrane is a blood separation membrane. This primary whole blood separation membrane is referred to herein, as Membrane-1. Membrane-1 contains a non-hemolytic surfactant, hemagglutinating agent, hemoglobin oxidizing agent, polymer, and buffer. Membrane-1 can be composed of one, or a combination of several, material(s) including, but not limited to, glass fiber, nylon, polyester, cellulose, cellulose acetate, nitrocellulose, polycarbonate, polyvinylidene difluoride, polyethersulfone, or polysulfone with a particle retention in the range of 2.0-5.0 µm. Membrane-1 is comprised of hemagglutinating agents, including but not limited to, anti-red blood cell antibodies, chitosan, hexadimethrine bromide, poly-L-lysine, poly-L-lysine hydrobromide, poly-D-lysine, poly-D-lysine hydrobromide, poly-DL-lysine hydrobromide, poly-L-arginine hydrochloride, poly(allylamine hydrochloride), poly(ethylenimine hydrochloride), diethylaminoethyl dextran, poly(n,n-dimethyl-3,5-dimethylene piperidinium chloride), or crude or purified lectins which agglutinate human type O erythrocytes efficiently such as those from *Phaseolus vulgaris, Maclura pomifera, Ulex europaeus*, and *Solanum tuberosum*. Additionally, the hemagglutinating agents can also be combined with a Neuraminidase, such as those from *Clostridium perfringens, Arthrobacter ureafaciens*, or *Streptococcus pneumonia*, to increase the hemagglutination efficiency of any lectins added to the primary blood separation membrane. The hemagglutinating agents can be immobilized together with a polymer, including but not limited to, hydroxypropyl cellulose, hydroxyethyl cellulose, poly(vinyl alcohol), dextran, gelatin, agarose, sodium carboxymethyl cellulose, xanthan gum, polyvinyl pyrrolidone, poly(1-vinylpyrrolidone-co-vinyl acetate), poly(vinyl acetate) or poly(methyl vinyl ether-alt-maleic anhydride).

As shown in FIG. 5, the test strip further comprises Membrane-2 M2. The plasma and remaining cells from the primary membrane M1 continue migrating vertically downward into the secondary membrane M2. The secondary whole blood separation membrane is referred to herein as Membrane-2. Membrane-2 is in direct contact with Membrane-1. Membrane-2 is composed of one, or a combination of several, material(s) including, but not limited to, glass fiber, nylon, polyester, cellulose, cellulose acetate, nitrocellulose, polycarbonate, polyvinylidene difluoride, polyethersulfone or polysulfone with a pore size in the range of 0.8-5.0 µm. Membrane-2 contains a non-hemolytic surfactant, polymer, and buffer.

In one non-limiting embodiment, Membrane-2 contains an immobilized preconditioning buffer in the pH range of 6.0 to 8.0. The optimal pH of PheDH can range from 10 to 11.5 depending on the variant. At the pH of optimal activity, the non-specific activity for endogenous L-tyrosine can interfere by as much as 100% in the blood Phe range of 0-6 mg/dL. The preconditioning of the biological fluid allows time for the homogenous mixing of the excipients while also buffering the biological fluid to a suitable pH for the enzymatic determination of Phe which simultaneously decreases the non-specific interaction PheDH has for L-tyrosine. The preconditioning of the biological solution to a lower pH suppresses the utilization of L-tyrosine as a substrate by PheDH.

The components on Membrane-2 are immobilized with a polymer. Examples of polymers include, but are not limited to, hydroxypropyl cellulose, hydroxyethyl cellulose, poly(vinyl alcohol), dextran, gelatin, agarose, sodium carboxymethyl cellulose, xanthan gum, polyvinyl pyrrolidone, poly(1-vinylpyrrolidone-co-vinyl acetate), poly(vinyl acetate) or poly(methyl vinyl ether-alt-maleic anhydride).

As shown in FIG. 5, the test strip further comprises Membrane-3 M3. The buffered fluid containing Phe travels to the tertiary membrane M3. The tertiary membrane is referred to herein as "the reagent membrane" or "Membrane-3". The reagent membrane is visually clean and smooth with submicron-sized pores thus providing excellent optical and reflective properties. Membrane-3 is composed of one, or a combination of several, material(s) including, but not limited to, nylon, cellulose, cellulose acetate, nitrocellulose, polycarbonate, polyethersulfone or polysulfone with a pore size in the range of 0.03-1.2 µm. This reagent membrane provides a uniform end-color in the read zone for precise detection. The reagent membrane contains a phenylalanine dehydrogenase (PheDH), a surfactant, polymer, buffer, an electron mediator, the cofactor β-Nicotinamide adenine dinucleotide or salts thereof, stabilizers, and a tetrazolium salt indicator. In one non-limiting embodiment, the PheDH is from *Thermoactinomyces intermedius, Bacillus badius, Sporosarcina ureae, Rhodococcus* sp. strain M4, or recombinant derivatives of the latter expressed in *Escherichia coli*. In one non-limiting embodiment, the electron mediator is a diaphorase, 1-methoxy-5-methylphenazinium methylsulfate (1-methoxy PMS), 1-methoxy-5-ethylphenazinium ethylsulfate (1-methoxy PES), or any combinations thereof. The components on Membrane-3 are immobilized with a polymer including, but not limited to, hydroxypropyl cellulose, hydroxyethyl cellulose, poly(vinyl alcohol), dextran, gelatin, agarose, sodium carboxymethyl cellulose, xanthan gum, polyvinyl pyrrolidone, poly(l-vinylpyrrolidone-co-vinyl acetate), poly(vinyl acetate) or poly(methyl vinyl ether-alt-maleic anhydride). The biological fluid slowly migrates vertically downward onto the reagent membrane. The end-color intensity of the reagent membrane can be measured in percent reflectance units on a handheld meter and converted to mg/dL or micromolar Phe through a preprogrammed curve set, calibrated against a laboratory reference instrument, or as an optical image measuring RGB values, which can then be calibrated against a laboratory reference instrument. The concentration of Phe can be determined by the end-color intensity at a given time or by kinetic rate determination. In one non-limiting embodiment, the reagent membrane is positioned facing a light emitting diode (LED) and photodiode to measure the end-color intensity of the reagent membrane or positioned facing a camera to image the end-color using Red/Green/Blue (RGB) values. In one non-limiting embodiment, the LED and photodiode can detect the end-color of a generated formazan that has a lambda max wavelength in the range of 500 nm and 700 nm for reflectance determination. Quantification of the analyte of interest can be achieved via percent reflectance versus a gold-standard reference instrument. The end-color can also be quantified using a camera to image the end-color intensity of the generated formazan. Quantification by image analysis can be calculated from RGB values.

Phenylalanine dehydrogenase in the presence of an electron mediator, the cofactor β-Nicotinamide adenine dinucleotide (NAD$^+$), and a tetrazolium salt indicator, the end-color intensity, or rate of color development, is proportional to the Phe concentration.

Suitable electron mediators or electron transfer agents include, but are not limited to, diaphorase (from *Clostridium kluyveri, Bacillus megaterium, Bacillus stearothermophilus*, Porcine Heart, or recombinant derivatives of the latter expressed in *Escherichia coli*), or non-enzymatic electron transfer agents, such as phenazine methosulfate (PMS), phenazine ethosulfate (PES), 1-methoxy-5-methylphenazinium methylsulfate (1-methoxy PMS) or 1-methoxy-5-ethylphenazinium ethylsulfate (1-methoxy PES), can all be used in the reduction of tetrazolium salts. Reaction kinetics and stability are the primary factors for selecting an electron transfer agent or electron mediator. For example, PMS is a good electron mediator because it has relatively fast reaction kinetics with most tetrazolium compounds described herein. PMS, however, is less stable in light than enzyme-based electron mediators such as diaphorase or other PMS derivatives. Diaphorase can be very stable in environmental conditions and, for that reason, is preferred when the cofactor $NAD^+$ is used.

PheDH catalyzes the oxidation of Phe and the reduction of $NAD^+$ to NADH. The NADH generated is utilized by diaphorase to reduce a tetrazolium salt to its corresponding colored formazan biproduct as in the reaction mechanism below:

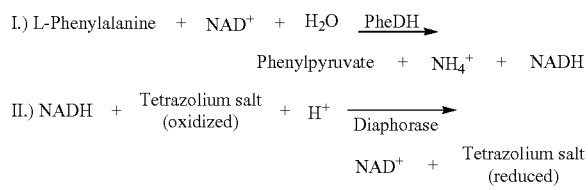

The "normal" range for Phe in the blood is 0-6 mg/dL. This invention demonstrates exceptional performance over the analytical range of 0 to 25 mg/dL (0-1513.4 µM) of Phe.

In practice, the test strip of the present invention determines Phe levels as a point-of-care test. The concentration of Phe in the blood is a critical parameter for neonatal determination of PKU, pre- and post-assessment for those with dietary restrictions, and monitoring after the administration of therapeutic medications.

The volume of blood used in the device, using a fingerstick whole blood sample, is less than 25 µL. This will allow for ease-of-use for the patient.

Figure 1A:
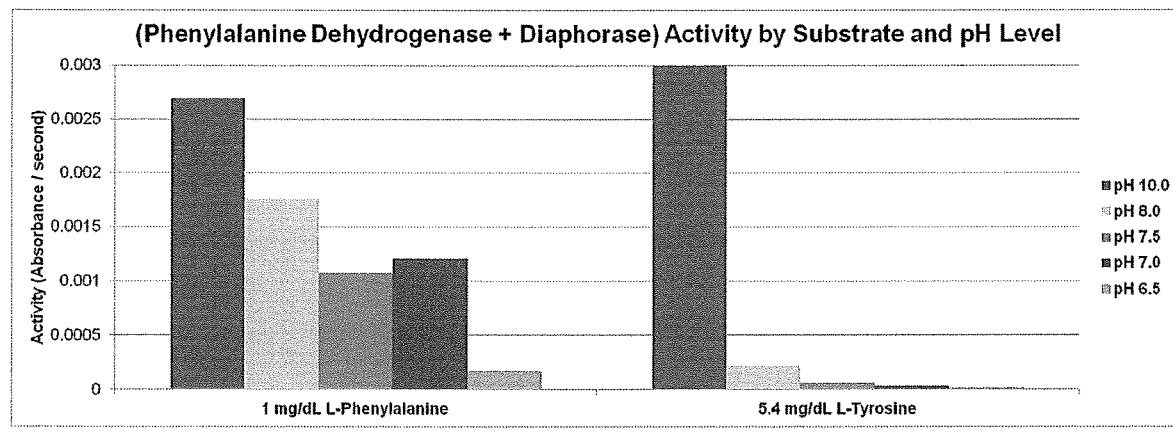
FIGS. 1A, 1B, and 1C show results of experiments using Diaphorase Type 1 and PheDH Type 1 which both have optimal activities at pH 10 (FIG. 1A and FIG. 1B). A second diaphorase (Diaphorase Type 2), with optimal activity at pH 8.0, was used in experiments at pH≤8.0 (FIG. 1C). As shown by these Figures, at pH>9.0, L-Tyrosine (5.4 mg/dL) can be used as a substrate for PheDH. Use of Diaphorase Type 2 at lower pH levels (7.0, 7.5, and 8.0) minimizes L-Tyrosine interference.
Figure 1B:
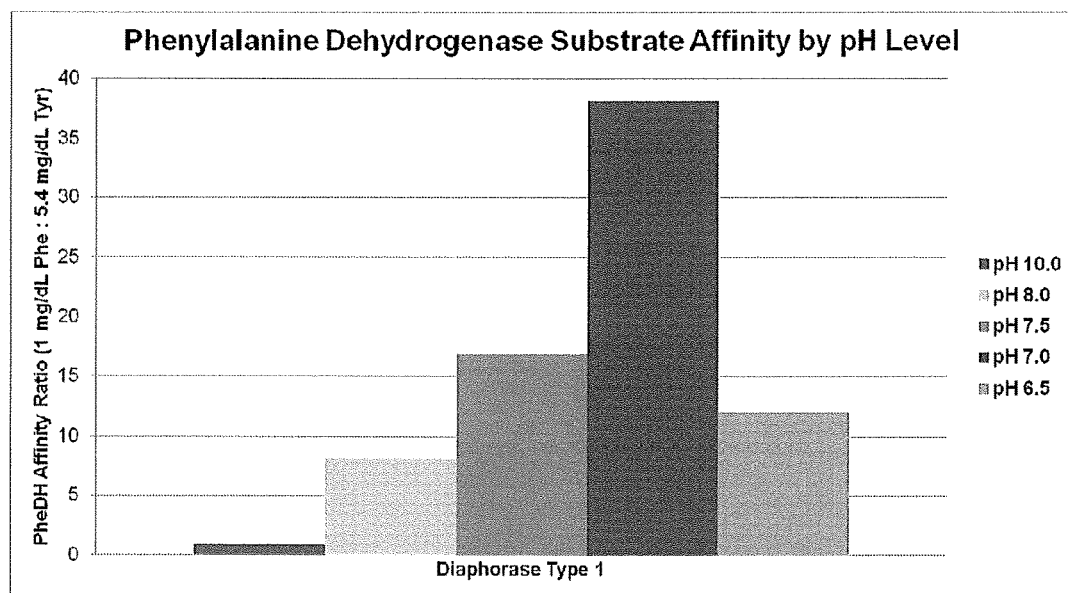
Figure 1C:
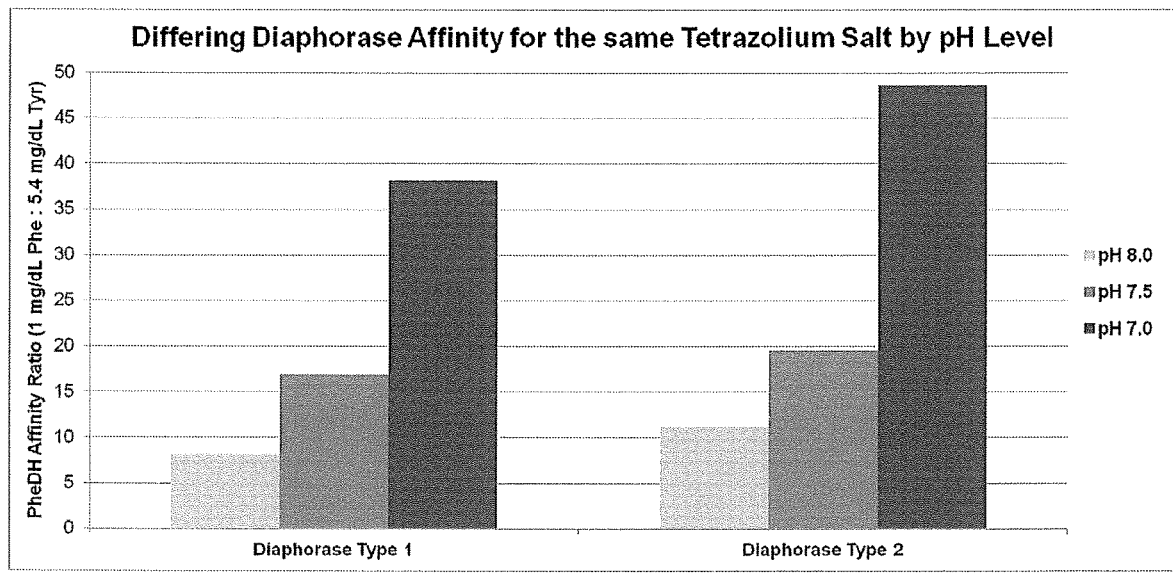

Two significant contributions of this invention are the ability to detect low concentration levels of Phe with a high degree of reliability (sensitivity), and the ability to discriminate between various concentrations of Phe over the clinically significant range. These are achieved in the present invention by the coupling of a diaphorase that performs extremely well at the low pH needed for the suppression of L-tyrosine interference, along with a highly sensitive tetrazolium salt indicator that acts as a good substrate for the preferred diaphorase. The harmonization of the diaphorase, at a given pH with a specific tetrazolium salt, provides the necessary sensitivity in the analytical range of 0 to 25 mg/dL Phe, while simultaneously suppressing endogenous L-tyrosine interference typically seen from phenylalanine dehydrogenase. See FIGS. 1A, 1B, and 1C.

The following non-limiting examples are provided to further illustrate the present invention.

EXAMPLES

Example 1: Determination of L-Phenylalanine in Human Whole Blood

An experiment was performed to demonstrate linearity of the present invention through the analytical range. The membranes were prepared as follows:

Spreading Layer
  Uncoated Mesh, Petex 07-200/39 (Sefar).
Working Solution, Membrane-1:
  A glass fiber membrane Grade 141 (Ahlstrom-Munksjö) was impregnated with the aqueous working solution of 0.2% Poly(vinyl alcohol) (M.W. 88-97K) (Alfa Aesar), 2.0% D-(+)-Sucrose (Carbosynth), 1.0% Chitosan (M.W. 15K) (Polysciences, Inc.), 10 mM Phosphate buffered saline (pH 6.5) (Santa Cruz Biotechnology), 1.0% Sodium Nitrite (Alfa Aesar) and 0.1% Triton X-305 (70%) (Dow Chemical). The membrane was dried at 50° C. for 30 minutes.

Working Solution, Membrane-2:
  Aqueous solutions of 100 mM Phosphate buffer, (Santa Cruz Biotechnology) pH 7.5 and 100 mM MES buffer, (TCI America) pH 6.0 were prepared. Each buffered solution contained 0.2% Triton X-305 (70%) (Dow Chemical) and 0.5% Poly(vinyl alcohol) (M.W. 88-97K) (Alfa Aesar). A 1.2 µm polysulfone membrane from GVS North America was coated with each of the solutions and dried at 50° C. for 15 minutes.

Stock Solution, Membrane-3:
  An aqueous solution containing 2.5% Hydroxypropyl cellulose (M.W. 100K) (Alfa Aesar), 10 mM Tris base buffer (TCI America) pH 8.0, 150 mM Potassium Chloride (TCI America), 2.0% D-(+)-Sucrose (Carbosynth), 0.1% D-Sorbitol (Carbosynth) and 0.1% Triton X-100 (Santa Cruz Biotechnology) was prepared.

Working Solution, Membrane-3:
  A solution comprised of 70 milligrams of β-Nicotinamide adenine dinucleotide monosodium salt dihydrate (Alfa Aesar), 1,500 units of Diaphorase, 1,500 units of Phenylalanine Dehydrogenase, 50 milligrams of Nitroblue tetrazolium chloride (Carbosynth), and 10 grams of Membrane-3 Stock Solution was prepared. A 0.22 µm polysulfone membrane (GVS North America) was immersed in the Membrane-3 Working Solution and dried at 50° C. for 15 minutes.

Test Strip Fabrication:
  A 15 mm ribbon of Duplocoll 5011® double-sided tape (Lohmann) was applied to Melinex 339 card stock (Tekra Corporation). Five-millimeter circular apertures were laser cut in the center of the 15 mm strip of tape. A 5 mm strip of the reagent layer (Membrane-3) was then laminated to the tape, positioned within the center of the aperture. Next, a 7 mm strip of Membrane-2 was placed over Membrane-3 and the edges were adhered to the Lohmann tape. A 10 mm strip of Membrane-1 was subsequently positioned over Membrane-2 and the edges were adhered to the Lohmann tape. Finally, a 14 mm strip of an uncoated mesh spreading layer, Petex 07-200/39 (Sefar), was placed over the stack of membranes and adhered to the Lohmann tape.

Whole blood was purchased from Biological Specialty Corporation and aliquoted into ten (1.8-mL) K2-EDTA microcentrifuge tubes. In two separate 3-mL tubes, the blood cells were allowed to settle and the plasma was removed. Three spiking solutions were prepared: A=1.0 mg/mL Phe, B=15.0 mg/mL Phe, and C=3.0 mg/mL L-tyrosine (Tyr). Table-1 lists the spiking volumes across the analytical range. Sixty microliters of samples 1 and 10 were aliquoted onto two dried blood spot (DBS) cards. These DBS cards were sent to ARUP Laboratories in Utah to determine the concentrations of Phe and Tyr by tandem mass spec analysis. Table-2 lists the results for Sample-1 and Sample-10. Table-1, Column-2 lists the volume of plasma that was removed and replaced with a plasma spiking solution. Table-1, Column-3 shows which spiking solution was used. Table-1, Column 4 shows the spiked Phe plus the endogenous Phe.

TABLE 1

| Sample: | Spike (μL) | A = 1 mg/dL Spiking Solution | B = 15 mg/dL Native + Sample Target (mg/dL) |
|---|---|---|---|
| #1 | Native Plasma | None | 0.90 |
| #2 | 20.0 | A | 2.90 |
| #3 | 3.3 | B | 5.90 |
| #4 | 7.0 | B | 11.40 |
| #5 | 9.0 | B | 14.30 |
| #6 | 10.0 | B | 15.90 |
| #7 | 12.0 | B | 18.90 |
| #8 | 14.5 | B | 22.65 |
| #9 | 17.5 | B | 27.10 |
| #10 | Sample #1 + 30 μL | C | 0.9 mg/dL Phe + 3.0 mg/dL Tyr |

TABLE 2

| Sample | Replicate | Analyte | Mass Spec (mg/dL) |
|---|---|---|---|
| #1 | Rep 1 | Phe | 0.90 |
| #1 | Rep 2 | Phe | 0.90 |
| #10 | Rep 1 | Tyr | 1.20 |
| #10 | Rep 2 | Tyr | 2.30 |
| #10 | Rep 3 | Phe | 1.30 |
| #10 | Rep 4 | Phe | 1.10 |

Each sample was measured at a wavelength of 530 nm after 3 minutes using a reflectance meter. Table-3, Column-3 list lists the mean percent reflectance of two test strip readouts. The values in Table-3, Column-2 (mg/dL) were plotted against the values in Table-3, Column-3 (% reflectance) to generate a $3^{rd}$ order polynomial (see FIG. 2).

TABLE 3

| Mass Spec μM | Mass Spec mg/dL | PKU NOW Mean % R | PKU NOW mg/dL | PKU NOW μM |
|---|---|---|---|---|
| 54.48 | 0.90 | 73.20 | 0.67 | 40.56 |
| 175.56 | 2.90 | 62.13 | 3.51 | 212.48 |
| 357.16 | 5.90 | 55.24 | 5.75 | 348.08 |
| 690.11 | 11.40 | 44.00 | 11.26 | 681.64 |
| 865.67 | 14.30 | 40.66 | 14.04 | 849.93 |
| 962.53 | 15.90 | 39.00 | 15.95 | 965.55 |
| 1138.08 | 18.80 | 37.30 | 18.55 | 1122.95 |
| 1371.15 | 22.65 | 33.70 | 25.50 | 1543.68 |
| 1640.54 | 27.10 | 32.40 | 27.37 | 1656.88 |
| 72.64 | 1.20 | 71.30 | 1.11 | 67.20 |

Figure 2:
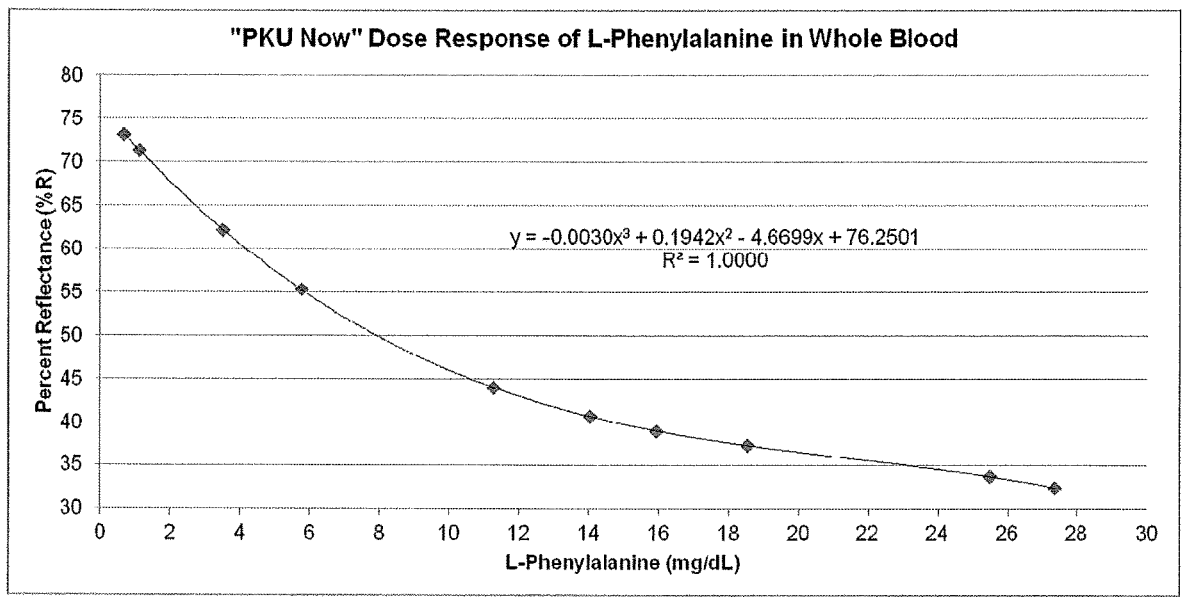
FIG. 2 is a curve generated from the percent reflectance values obtained from spiked blood samples.

FIG. 2 shows the curve generated from the percent reflectance values obtained from each spiked blood sample.

Figure 3:
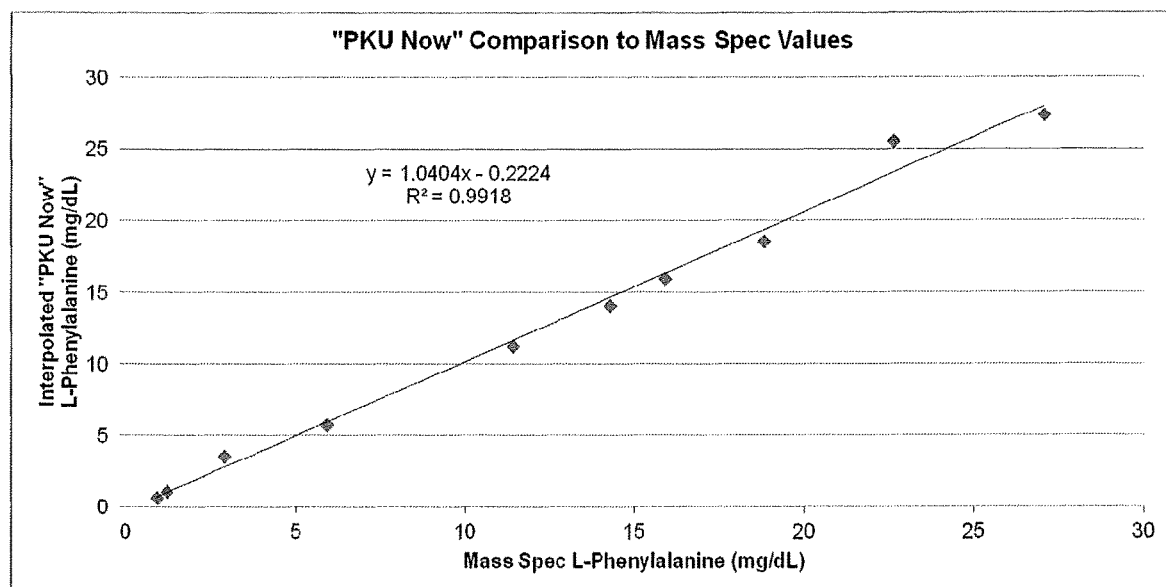
FIG. 3 is a graph showing the correlation of the mg/dL Phe values obtained from the "PKU Now" with the mg/dL Phe values obtained from mass spec analysis.

The concentrations of Phe in mg/dL were then calculated using the equation $y=0.003x^3+0.1942x^2-4.6699x+76.25$. Table-3, Column-4 lists these calculated mg/dL values. Finally, the calculated values were plotted against the tandem mass spec values. FIG. 3 shows a linear regression revealing the correlation of the mg/dL Phe values obtained from the "PKU Now" assay of the present invention with the mg/dL Phe values obtained from mass spec analysis.

Example 2 Determination of L-Phenylalanine in Human Whole Blood with Spiked L-Tyrosine Across the Analytical Range for L-Phenylalanine Six whole blood samples were spiked with Phe (Group-1) across the analytical range (Table-4, Column-1). Half of the volume from each of the six whole blood samples was removed to create a second group of samples (Group-2). Each of these samples was further spiked to a concentration of 3 mg/dL Tyr. The samples in Group-1 were within the analytical range of Phe, while the samples in Group-2 contained Phe as well as Tyr at a concentration 3 mg/dL (upper limit for Tyr). Both groups of samples were assayed using a pH of 6.0 and a pH of 8.5 on Membrane-2.

Figure 4:
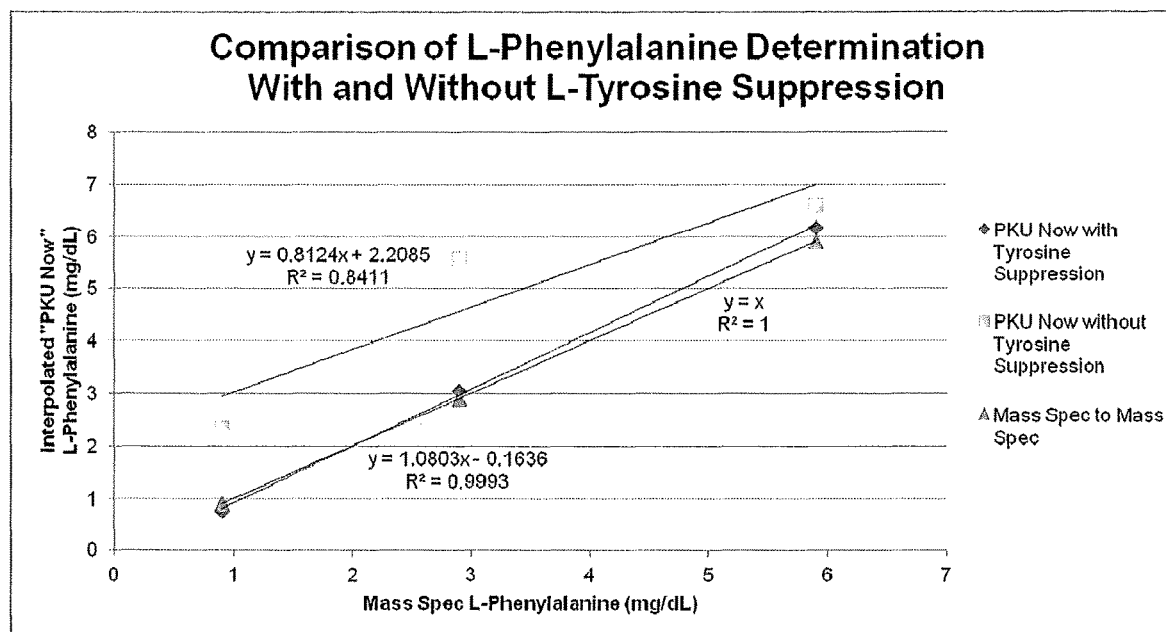
FIG. 4 is a graph showing the concordance of the "PKU Now" with the Mass Spec Phe values when the L-Tyrosine suppression technology is utilized.

FIG. 4 shows the concordance of PKU Now with the Mass Spec Phe values when the L-Tyrosine suppression technology is utilized.

TABLE 4

| mg/dL Phe | pH 6.0, Phe Only | pH 6.0, Phe + Tyr | pH 8.5, Phe + Tyr |
|---|---|---|---|
| 0.9 | 75.20 | 75.65 | 65.60 |
| 2.9 | 62.90 | 61.55 | 50.05 |
| 5.9 | 46.00 | 47.90 | 46.50 |
| 11.4 | 38.85 | 38.55 | 36.95 |
| 18.9 | 30.35 | 30.95 | 30.60 |
| 27.1 | 24.75 | 28.05 | 26.75 |

Table-4, Column-1 lists the spiked Phe concentration in mg/dL. Table-4, Column-2 lists the mean percent reflectance (% R) of the test strip duplicates using Membrane-2 at pH 6.0 with the samples that were spiked with Phe alone. Table-4, Column-3 lists the % R of the test strip duplicates using Membrane-2 at pH 6.0 with the samples that were spiked with both Phe and Tyr. Table-4, Column-4 lists the mean % R of the test strip duplicates using Membrane-2 at pH 8.5 with the same samples as in Column-3. Graph-3 is a $3^{rd}$ order polynomial ($y=0.0073x^3+0.4014x^2-7.5891x+81.182$) generated by plotting the calculated concentration of Phe (Table-4 Column-1) against the % R measured from the reaction (Table-4 Column-2).

TABLE 5

| mg/dL Phe | Calculated Phe Values (mg/dL) | |
|---|---|---|
| | pH 6.0, Tyr Suppression | pH 8.5, No Tyr Suppression |
| 0.9 | 0.7590 | 2.3276 |
| 2.9 | 3.0523 | 5.5839 |
| 5.9 | 6.1768 | 6.5940 |
| 11.4 | 9.7665 | 10.7280 |
| 18.9 | 21.6372 | 22.3059 |
| 27.1 | 25.1761 | 26.1021 |

Table-5, Column-2 contains the interpolated Phe (mg/dL) for Membrane-2 at pH 6.0. Table-5, Column-3 contains the interpolated values for Membrane-2 at pH 8.5. The data reveals that at pH 8.5, the addition of Tyr to the whole blood samples substantially over-recovers (2.32 and 5.59 mg/dL) at the lower Phe levels of 0.9 and 2.9 mg/dL, respectively. However, when the non-specific activity suppression technology is used (pH 6.0), the Phe mg/dL values fall very close to the actual, 0.759 and 3.05 mg/dL, respectively. The data also shows that with an increase in Phe concentration, the interference of Tyr becomes minimal, but still shows a positive bias across the analytical range. It is critical to suppress Tyr interference in order to identify true normal patients, to provide patients with accurate Phe values for monitoring their Phe intake, and to establish an accurate Phe calibration curve for any analyzer. The offset of MS/MS mg/dL Phe results (Table-5, Column-1) to that of calculated mg/dL Phe (Table-5, Column-2) is a function of different curve sets.

What is claimed is:

1. A device for quantitatively measuring L-phenylalanine in a biological sample, said device including a test strip comprising from top to bottom in following order:
   a sample spreading layer;
   a primary whole blood separation membrane;
   a secondary whole blood separation membrane with an immobilized preconditioning buffer in the pH range of 6.0 to 8.0; and
   an optical, colorimetric, reagent membrane for L-phenylalanine detection with suppression of endogenous L-tyrosine interference up to 6 mg/dL.

2. The device of claim 1 further comprising a light emitting diode (LED) and photodiode or camera positioned adjacent to the test strip to detect the end-color intensity of the reagent membrane indicative of the L-phenylalanine concentration in the biological sample.

3. The device of claim 1 wherein the sample spreading layer comprises a nylon or polyester mesh with a pore size in the range of 10-300 μm that distributes the biological sample laterally and evenly across a surface of the primary whole blood separation membrane.

4. The device of claim 1 wherein the primary whole blood separation membrane is composed of glass fiber, nylon, polyester, cellulose, cellulose acetate, nitrocellulose, polycarbonate, polyvinylidene difluoride, polyethersulfone, polysulfone or combinations thereof, with a particle retention in the range of 2-5 μm.

5. The device of claim 4 wherein the primary whole blood separation membrane is treated with:
   a buffer, a non-hemolytic surfactant, a polymer, and hemagglutinating agents to prevent contamination of red blood cells into the reagent membrane; and
   an agent that oxidizes hemoglobin to methemoglobin.

6. The device of claim 1 wherein the secondary whole blood separation membrane is composed of glass fiber, nylon, polyester, cellulose, cellulose acetate, nitrocellulose, polycarbonate, polyvinylidene difluoride, polyethersulfone, polysulfone or combinations thereof, with a pore size in ranging from 0.8-5.0 μm.

7. The device of claim 6 wherein the secondary whole blood separation membrane is treated with a preconditioning buffer at a concentration of 25-150 mM adjusted to pH 6.0-8.0 and a non-hemolytic surfactant which are both immobilized onto the membrane using a polymer.

8. The device of claim 1 wherein the reagent membrane is optically smooth, comprised of nylon, cellulose, cellulose acetate, nitrocellulose, polycarbonate, polyethersulfone, polysulfone or combinations thereof, with a pore size of less than or equal to 1.2 μm, and is buffered to a pH of 6.0-8.0.

9. The device of claim 8 wherein the reagent membrane is treated with a buffer, surfactant, stabilizers, colorimetric indicator, a cofactor, phenylalanine dehydrogenase, and an electron mediator, all of which are immobilized on the reagent membrane using a polymer.

10. The device of claim 9 wherein the phenylalanine dehydrogenase is derived from *Thermoactinomyces intermedius, Bacillus badius, Sporosarcina ureae, Rhodococcus* sp. strain M4, or recombinant derivatives thereof expressed in *Escherichia coli*.

11. The device of claim 9 wherein the electron mediator is a diaphorase with an optimum pH activity in the range of 6.0 and 8.5.

12. The device of claim 11 wherein the diaphorase is derived from *Clostridium kluyveri, Bacillus megaterium, Bacillus stearothermophilus*, Porcine Heart, or recombinant derivatives thereof expressed in *Escherichia coli*.

13. The device of claim 9 wherein the colorimetric indicator is a tetrazolium salt that produces a colored formazan upon reduction, with the formazan having a lambda max wavelength between 500 nm and 700 nm.

14. The device of claim 1 wherein the layer and membranes of the test strip are adhered to a base material through lamination with adhesives or through compression in a cassette.

15. The device of claim 1 wherein the test strip allows for zero to six percent bias in the hematocrit range of 32-60% through the analytical range of 0-25 mg/dL L-phenylalanine.

16. A method for quantitatively measuring L-phenylalanine in a biological sample, said method comprising applying the biological sample to the device of claim 1 and measuring L-phenylalanine in the biological sample.

17. The method of claim 16 wherein the biological sample applied is less than 25 μL.

18. The method of claim 16 wherein the reagent membrane of the test strip is positioned facing a light emitting diode (LED) and photodiode to measure the end-color intensity of the reagent membrane indicative of L-phenylalanine in the biological sample.

19. The method of claim 16 wherein the reagent membrane of the test strip is positioned facing a camera to image the end-color and quantified using Red/Green/Blue (RGB) values.

20. The method of claim 16 is used in the diagnosis of phenylketonuria (PKU).

* * * * *